US006106547A

United States Patent [19]

Huei-Jung

[11] Patent Number: 6,106,547

[45] Date of Patent: Aug. 22, 2000

[54] HOT/COLD DUAL-MOLD SKIN TREATMENT APPARATUS

[76] Inventor: Lien Huei-Jung, P.O. Box 24-108, Taipei, Taiwan

[21] Appl. No.: 09/158,620

[22] Filed: Sep. 22, 1998

[51] Int. Cl.[7] ..................................................... A61F 7/00

[52] U.S. Cl. ........................................ 607/96; 128/200.14

[58] Field of Search .............................. 607/96, 108–109; 128/200.14, 200.2; 261/DIG. 65; 4/526, 537

[56] References Cited

U.S. PATENT DOCUMENTS

| | | | |
|---|---|---|---|
| 4,369,776 | 1/1983 | Roberts | 128/200.14 |
| 5,010,905 | 4/1991 | Snyder et al. | 132/272 |

*Primary Examiner*—Linda C. M. Dvorak
*Assistant Examiner*—David M. Ruddy
*Attorney, Agent, or Firm*—Dougherty & Troxell

[57] ABSTRACT

A hot/cold dual-mode skin treatment apparatus includes a housing holding a skin treatment solution in a water trough therein, a barrel mounted in a vertical through hole on the housing, an atomizer mounted in the water trough and controlled to oscillate the skin treatment solution into a fine spray of skin treatment solution. A fan and an air duct connected between the fan and the bottom end of the barrel for guiding currents of air from the fan to the barrel to carry the fine spray of skin treatment solution out of the housing. A spray nozzle assembly is mounted in the barrel on the housing to guide out the fine spray of skin treatment solution, and electrical heater is mounted in the spray nozzle assembly and controlled to heat the fine spray of skin treatment solution into steam.

2 Claims, 5 Drawing Sheets

HOT/COLD DUAL-MOLD SKIN TREATMENT APPARATUS

BACKGROUND OF THE INVENTION

The present invention relates to a skin treatment apparatus, and more particularly to a hot/cold dual-mode skin treatment apparatus that can be controlled to eject a cold spray of skin treatment solution or a hot spray of skin treatment solution for treating the skin of a person.

It is well known that applying a hot compress to a part of the body positively stimulates the circulation of blood, and simultaneously relaxes the muscles and releases pains. According to conventional methods, a hot compress is achieved by dipping a towel in hot water and then covering the towel over the area of body to be treated, or directly applying steam to the body. The former method is less effective because the temperature of the towel drops quickly. The later method is more effective, however it takes much time in heating water into steam. Furthermore, it is also known that applying fine drops of water to the skin can stimulate the circulation of blood without causing an irritation to the skin.

SUMMARY OF THE INVENTION

It is one object of the present invention to provide a skin treatment apparatus which provides a cold temperature treatment mode and a hot temperature treatment mode. It is another object of the present invention to provide a hot/cold dual-mode skin treatment apparatus which can be conveniently operated to provide a cold spray of skin treatment solution or a hot spray of skin treatment solution for treating the skin of a person. According to the invention, the hot/cold dual-mode skin treatment apparatus comprises a housing holding a skin treatment solution in a water trough therein, a barrel mounted in a vertical through hole on the housing, an atomizer mounted in the water trough and controlled to oscillate the skin treatment solution into a fine spray of skin treatment solution, fan means, an air duct connected between the fan means and the bottom end of the barrel for guiding currents of air from the fan means to the barrel to carry the fine spray of skin treatment solution out of the housing, a spray nozzle assembly mounted in the barrel on the housing to guide out the fine spray of skin treatment solution, and electrical heating means mounted in the spray nozzle assembly and controlled to heat the fine spray of skin treatment solution into steam.

DETAILED DESCRIPTION OF THE PREFERRED EMBODIMENT

Figure 1:
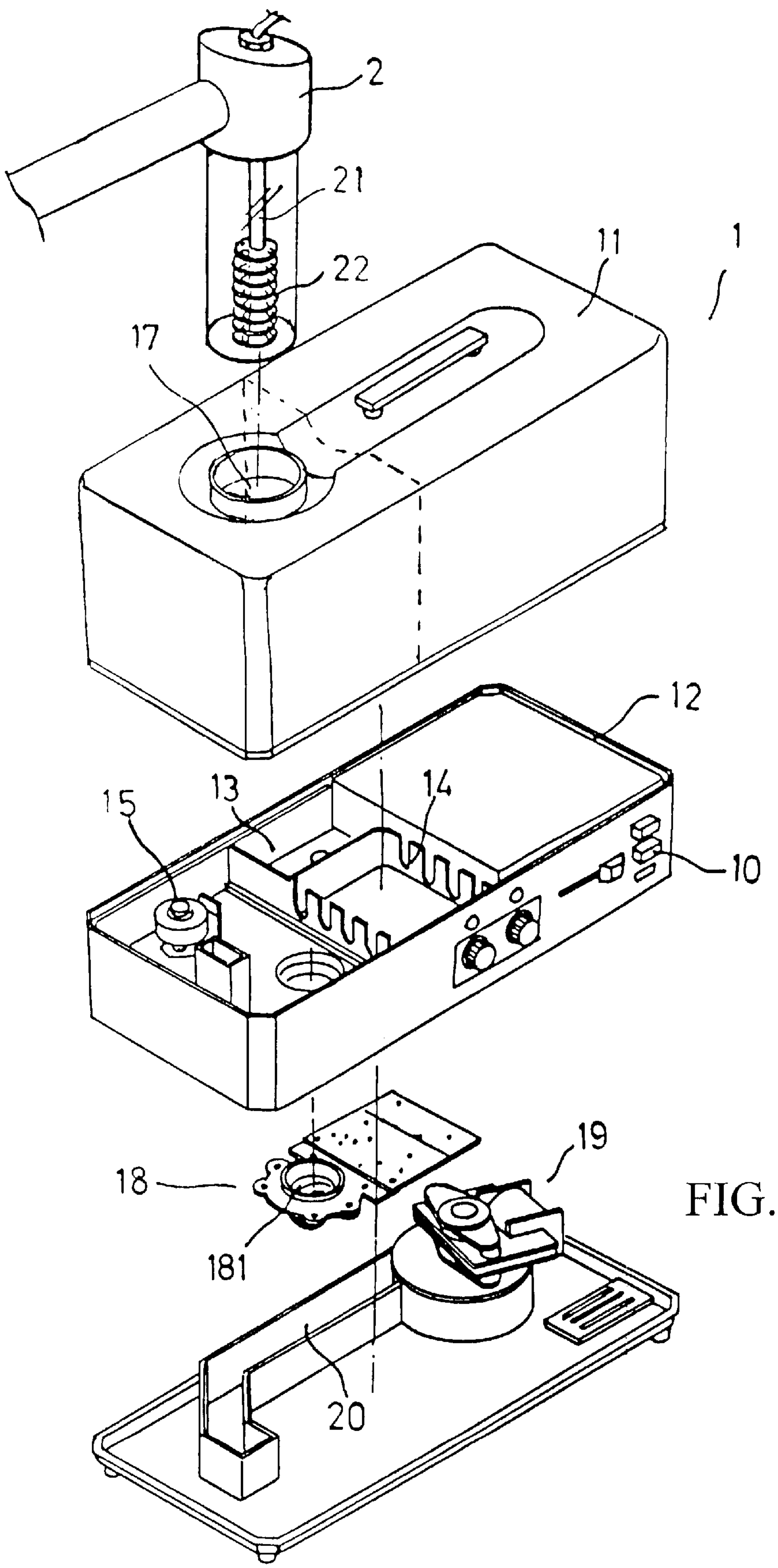
FIG. 1 is an exploded view of a hot/cold dual-mode skin treatment apparatus according to the present invention.
Figure 2:
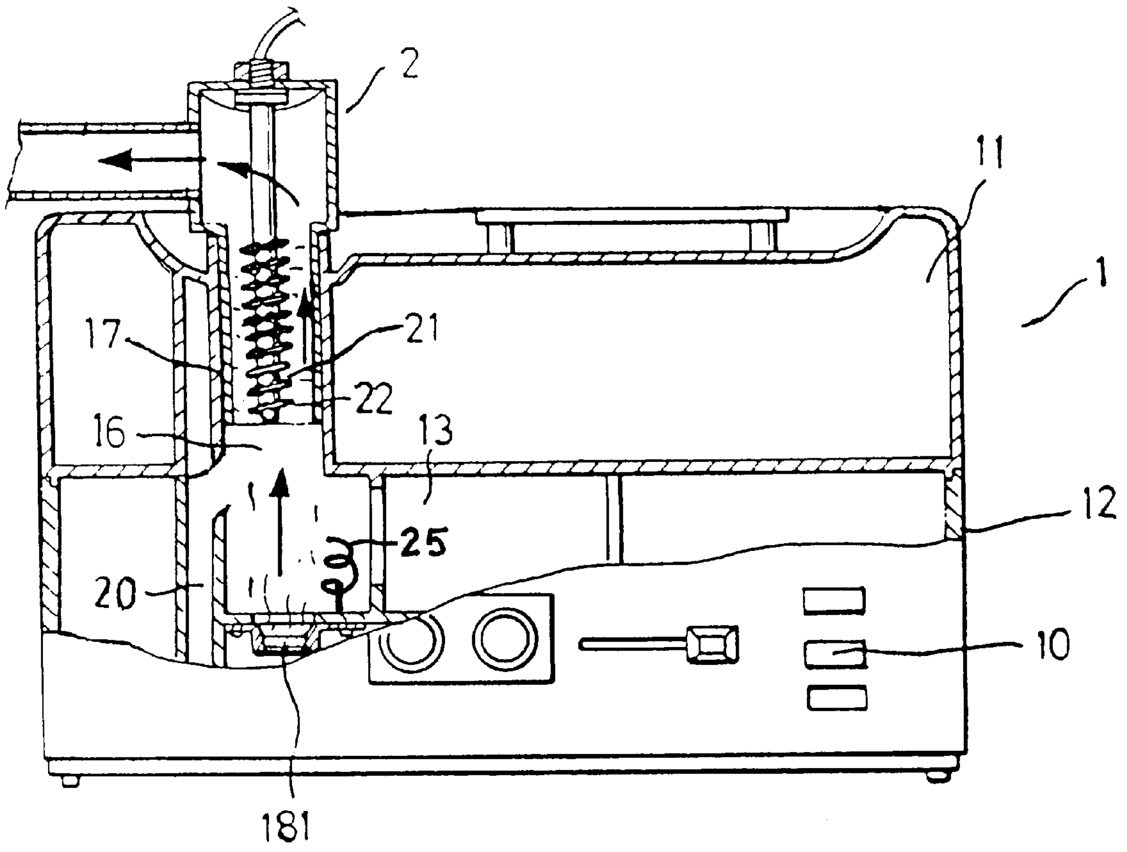
FIG. 2 is a sectional view of the hot/cold dual-mode skin treatment apparatus shown in FIG. 1.

Referring to FIGS. 1 and 2, a hot/cold dual-mode skin treatment apparatus in accordance with the present invention comprises a shell 1, and a spray nozzle assembly 2. The shell 1 comprises a water reservoir 11 in which a skin treatment solution is filled. A bottom case 12 is fastened to the shell 1 at the bottom, defining a water trough 13 in communication with the water reservoir 11. A water distributor 14 and a water level detector 15 are provided in the water trough 13. The water distributor 14 buffers the flowing velocity of water. The water level detector 15 detects the level of water in the water trough 13. A barrel 17 is mounted in a through hole 16 on the shell 1 in communication with the water trough 13. An atomizer 18 mounted in the through hole 16 at the bottom. The atomizer 18 is comprised of an oscillator 181. When the oscillator 181 is operated, water is oscillated into fine drops. An electrical heater 25 is mounted in the water trough 13, and controlled to heat water in the water trough 13. A fan 19 is mounted inside the bottom case 12. An air duct 20 is connected between the fan 19 and the through hole 16. The spray nozzle assembly 2 is mounted in the barrel 17, comprising an electrical heating element 21, and fins 22 around the electrical heating element 21. A control switch 10 is mounted on the outside of the bottom case 12 for controlling the operation of the electrical heating element 21, the electrical heater 25 and the fan 19.

Figure 3:
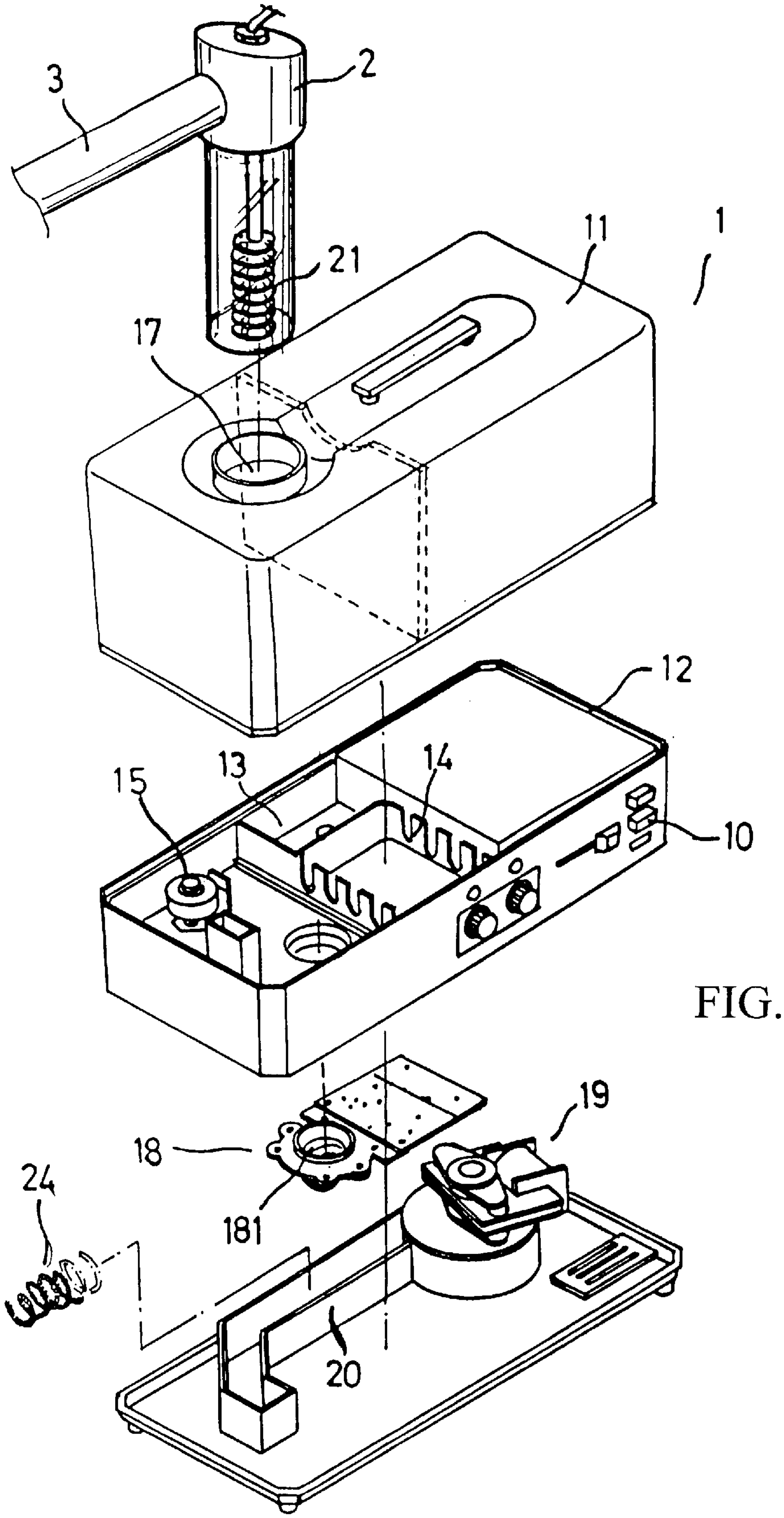
FIG. 3 is an exploded view of an alternate form of the hot/cold dual-mode skin treatment apparatus according to the present invention.
Figure 4:
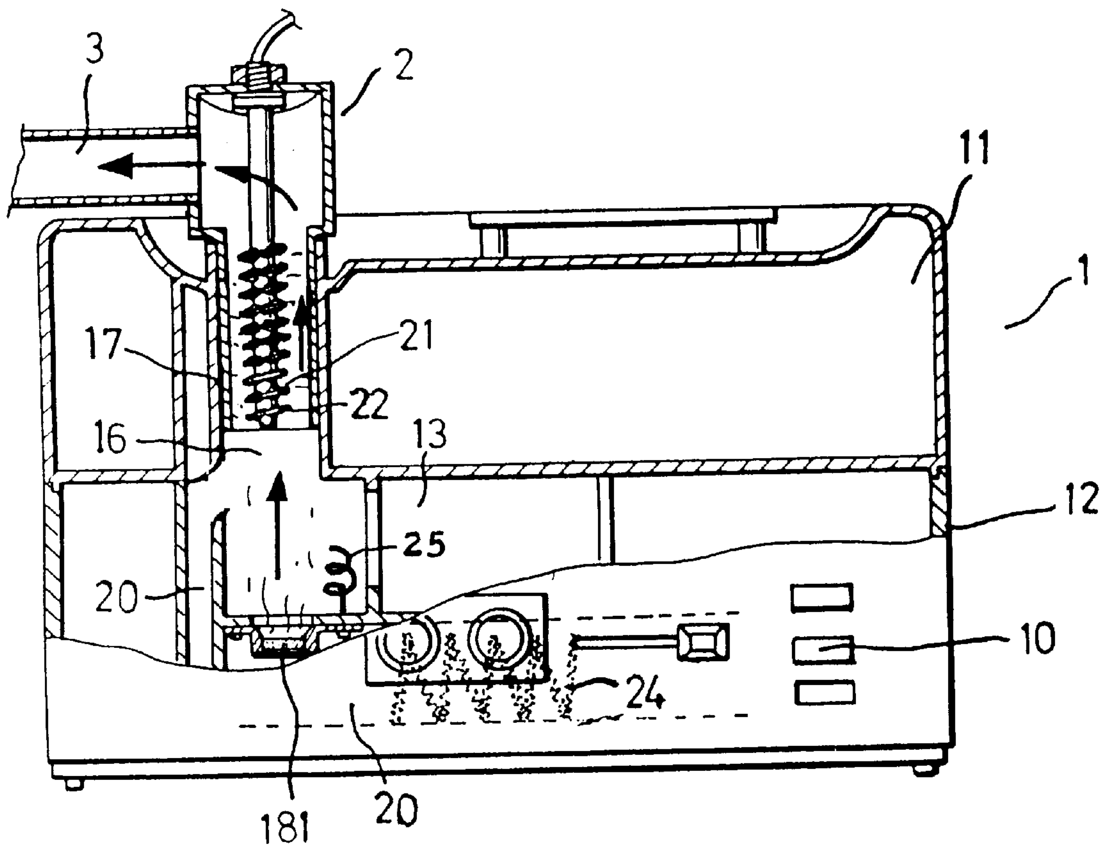
FIG. 4 is a sectional view of the hot/cold dual-mode skin treatment apparatus shown in FIG. 3.

Referring to FIGS. 3 and 4, a heat dissipating device 24 is installed in the air duct 20 within the bottom case 12 for quick transmission of heat.

Figure 5:
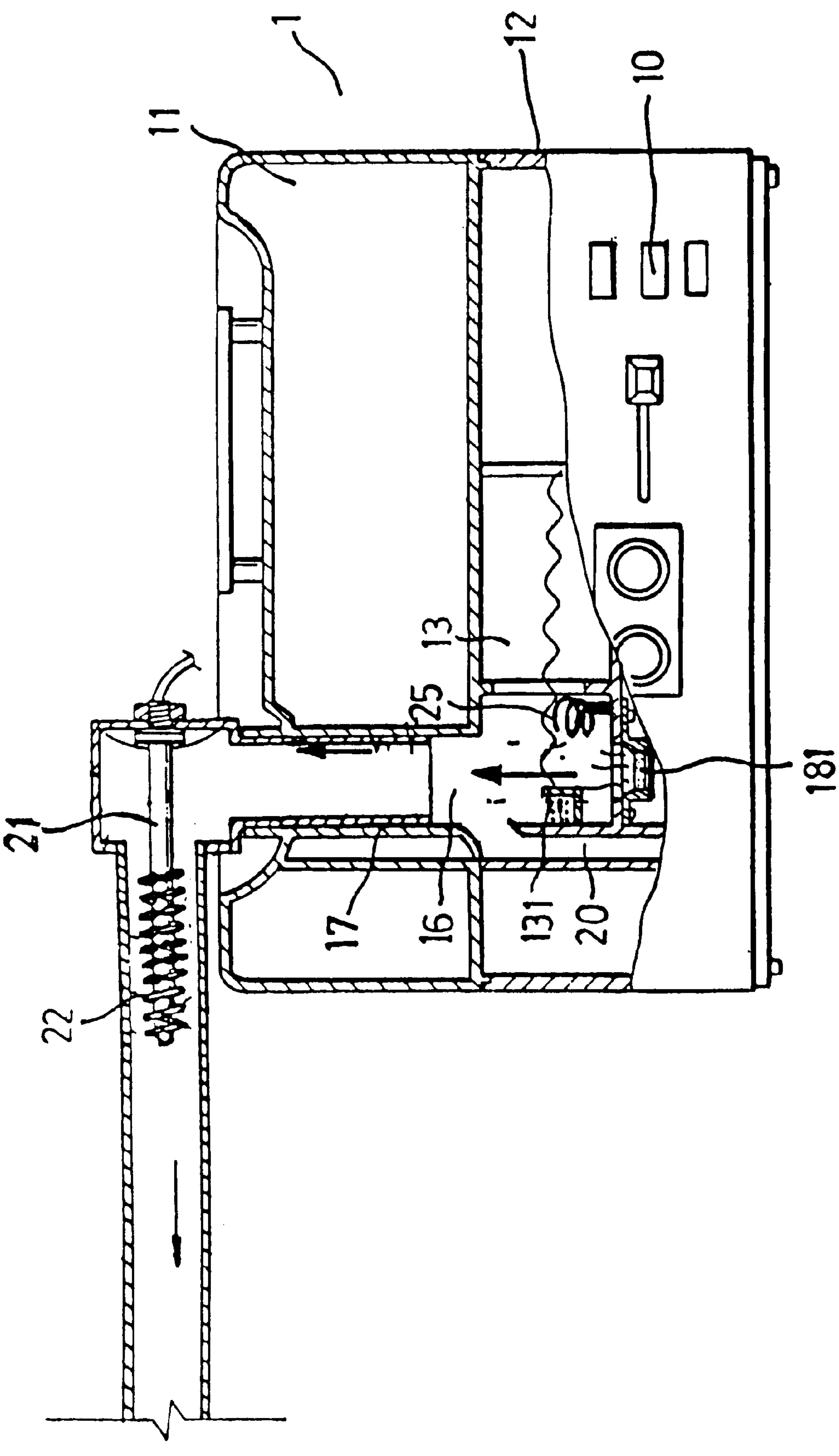
FIG. 5 is a sectional view of another alternate form of the hot/cold dual-mode skin treatment apparatus according to the present invention.

Referring to FIG. 5, a solution dispenser 131 may be mounted in the water trough 13 of the bottom case 12. When fine drops of water pass through holes on the solution dispenser 131, a skin treatment solution is carried out of the solution dispenser 131.

When in use, a skin treatment solution is filled in the solution dispenser 131 or mixed in water in the water reservoir 11. When power is turned on, the oscillator 181 of the atomizer 18 is started to oscillate water in the water trough 13, causing a mist of low temperature (about 20~22° C.) skin treatment solution to be produced and carried out of the spray nozzle assembly 2 by currents of air from the fan 19 for treating the skin of a person. For a steam treatment, the control switch 10 is operated to turn on the electrical heating element 21 and the electrical heater 25 to heat skin treatment solution into steam. The steam of skin treatment solution thus produced is then carried out of the spray nozzle assembly 2 by currents of air from the fan 19 for treating the skin.

It is to be understood that the drawings are designed for purposes of illustration only, and are not intended as a definition of the limits and scope of the invention disclosed.

What the invention claimed is:

1. A hot/cold dual-mode skin treatment apparatus comprising:

a housing, having a water reservoir holding a skin treatment solution, a water trough in communication with said water reservoir, a water level detector which detects the water level in said water trough, and a vertical through hole;

a fan;

an air duct connected between said fan and said through hole for guiding currents of air from said fan to said through hole to carry the fine spray of skin treatment solution out of said through hole;

a spray nozzle assembly mounted in the through hole on said housing to guide out the fine spray of skin treatment solution;

a first electrical heater located in said water trough to heat water in the trough; and, a second electrical heater located in the spray nozzle assembly to heat said fine spray of skin treatment solution into steam.

2. The hot/cold dual-mode skin treatment apparatus of claim 1 further comprising a dispenser mounted in said water trough at the bottom end of said through hole to dispense a chemical in the skin treatment solution in said water trough.

* * * * *